US008693758B2

(12) United States Patent
Klingenbeck

(10) Patent No.: US 8,693,758 B2
(45) Date of Patent: Apr. 8, 2014

(54) IMAGING METHOD FOR ENHANCED VISUALIZATION OF VESSELS IN AN EXAMINATION REGION OF A PATIENT AND MEDICAL SYSTEM FOR PERFORMING THE METHOD

(75) Inventor: Klaus Klingenbeck, Aufseβ (DE)

(73) Assignee: Siemens Aktiengesellschaft, Munich (DE)

( * ) Notice: Subject to any disclaimer, the term of this patent is extended or adjusted under 35 U.S.C. 154(b) by 219 days.

(21) Appl. No.: 13/094,855

(22) Filed: Apr. 27, 2011

(65) Prior Publication Data
US 2011/0268333 A1 Nov. 3, 2011

(30) Foreign Application Priority Data

Apr. 30, 2010 (DE) .......................... 10 2010 018 872

(51) Int. Cl.
G06K 9/00 (2006.01)
(52) U.S. Cl.
USPC ........... 382/131; 382/128; 382/132; 600/425; 600/424; 600/434; 600/431
(58) Field of Classification Search
USPC .......... 382/131, 132, 128; 600/425, 424, 434, 600/431
See application file for complete search history.

(56) References Cited

U.S. PATENT DOCUMENTS

| 6,370,421 | B1 * | 4/2002 | Williams et al. | 600/433 |
| 6,923,768 | B2 * | 8/2005 | Camus et al. | 600/463 |
| 7,340,082 | B2 * | 3/2008 | Janssen et al. | 382/128 |
| 7,500,784 | B2 | 3/2009 | Grebner et al. | |
| 7,792,343 | B2 * | 9/2010 | Pekar | 382/128 |
| 7,839,403 | B2 * | 11/2010 | Heigl et al. | 345/423 |
| 8,050,471 | B2 * | 11/2011 | Mielekamp et al. | 382/128 |
| 8,060,186 | B2 * | 11/2011 | Mohamed et al. | 600/427 |
| 2003/0125622 | A1 * | 7/2003 | Schweikard et al. | 600/437 |
| 2004/0077942 | A1 * | 4/2004 | Hall et al. | 600/428 |
| 2005/0004449 | A1 * | 1/2005 | Mitschke et al. | 600/424 |
| 2005/0288578 | A1 * | 12/2005 | Durlak | 600/434 |
| 2006/0184066 | A1 * | 8/2006 | Karmonik et al. | 600/587 |
| 2006/0262970 | A1 * | 11/2006 | Boese et al. | 382/131 |

(Continued)

FOREIGN PATENT DOCUMENTS

| DE | 10 2006 056 679 A1 | | 6/2008 |
| WO | WO 2009/127972 | * | 4/2009 |
| WO | WO 2010048434 | * | 4/2010 |

OTHER PUBLICATIONS

"Souha Aouadi, Laurent Sarry" "Accurate and precise 2D-3D registration based on X-ray intensity", "Elsivier Jun. 27, 2007".*

(Continued)

Primary Examiner — Stephen R Koziol
Assistant Examiner — Shaghayegh Azima

(57) ABSTRACT

An imaging method for enhanced visualization of vessels in an examination region of a patient, in particular during an intervention, is proposed. A 3D reconstruction image of the examination region is generated using a preoperatively recorded 3D image dataset of the examination region. At least one current 2D fluorescence image of the examination region is recorded by a fluorescence angiography. The vessels are identified. The 3D image dataset with the image dataset of the 2D fluorescence or ultrasound image is registered based on the result of the identification. The 3D reconstruction image and the 2D image are overplayed. The overlaid images are 3D played back.

9 Claims, 4 Drawing Sheets

(56) References Cited

U.S. PATENT DOCUMENTS

| | | | |
|---|---|---|---|
| 2007/0053481 A1* | 3/2007 | Boese | 378/4 |
| 2007/0206848 A1* | 9/2007 | Ohishi | 382/154 |
| 2008/0207997 A1* | 8/2008 | Higgins et al. | 600/114 |
| 2008/0242971 A1* | 10/2008 | Klingenbeck-Regn | 600/407 |
| 2008/0249400 A1* | 10/2008 | Golijanin et al. | 600/431 |
| 2008/0273784 A1* | 11/2008 | Pfister | 382/131 |
| 2009/0088830 A1* | 4/2009 | Mohamed et al. | 623/1.11 |
| 2009/0091567 A1* | 4/2009 | Fu et al. | 345/419 |
| 2009/0148009 A1* | 6/2009 | Mielekamp et al. | 382/128 |
| 2009/0198126 A1* | 8/2009 | Klingenbeck-Regn | 600/426 |
| 2009/0257559 A1* | 10/2009 | Urushiya et al. | 378/98.12 |
| 2009/0306511 A1* | 12/2009 | Yamagata | 600/447 |
| 2011/0260725 A1* | 10/2011 | Mordini et al. | 324/309 |
| 2011/0275933 A1* | 11/2011 | Dey et al. | 600/428 |
| 2011/0306877 A1* | 12/2011 | Dvorsky et al. | 600/431 |

OTHER PUBLICATIONS

Zollei, L.; Grimson, E.; Norbash, A.; Wells, W., "2D-3D rigid registration of X-ray fluoroscopy and CT images using mutual information and sparsely sampled histogram estimators," Computer Vision and Pattern Recognition, 2001. CVPR 2001. Proceedings of the 2001 IEEE Computer Society Conference on, vol. 2, No., pp. II-696,II-703 vol. 2, 2001.*

Souha Aouadi; Laurent Sarry,"Accurate and precise 2D-3D registration based on X-ray intensity", Computer Vision and Image Understanding 110 (2008) 134-151.*

WIPPER, Validierung der Fluoreszenzangiographie zur intraoperativen Beurteilung und Quantifizierung der Myokardperfusion, Dissertation, Medical faculty of the Ludwig-Maximilians University of Munich, Germany, 2006, pp. 1-98.

* cited by examiner

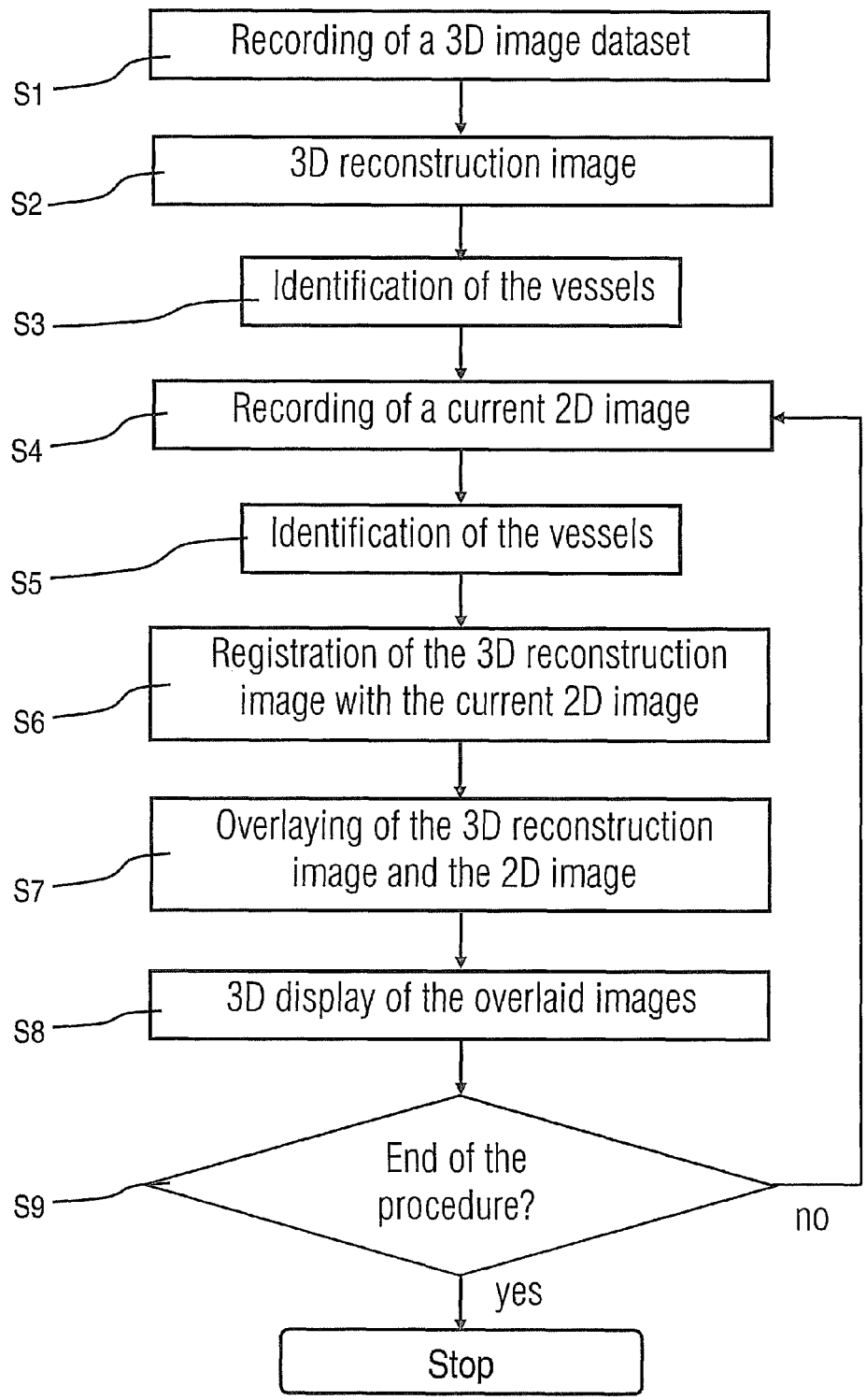

IMAGING METHOD FOR ENHANCED VISUALIZATION OF VESSELS IN AN EXAMINATION REGION OF A PATIENT AND MEDICAL SYSTEM FOR PERFORMING THE METHOD

CROSS REFERENCE TO RELATED APPLICATIONS

This application claims priority of German application No. 10 2010 018 872.7 filed Apr. 30, 2010, which is incorporated by reference herein in its entirety.

FIELD OF THE INVENTION

The invention relates to an imaging method for enhanced visualization of vessels in an examination region of a patient, in particular during an intervention, as well as to a medical system for performing the method.

BACKGROUND OF THE INVENTION

Three-dimensional digital subtraction rotation angiography (3D DSA rotation angiography) is a standard method for assessing the vascular anatomy before and during interventions. In digital subtraction angiography (DSA), mask images (images without contrast agent) and fill images (images with contrast agent) are first generated and then subtracted from one another so that only the changes over time induced by the contrast agent and reproducing the vessels are obtained.

Such a C-arm X-ray system for digital subtraction angiography, as shown by way of example in FIG. 1, has for example a C-arm 2 which is rotatably mounted on a stand in the form of a six-axis industrial or articulated arm robot 1 and at the ends of which are mounted an X-ray radiation source, for example an X-ray tube assembly 3 with X-ray tube and collimator, and an X-ray image detector 4 as image recording unit.

The articulated arm robot 1 known for example from U.S. Pat. No. 7,500,784 B2, which preferably has six axes of rotation and hence six degrees of freedom, enables the C-arm 2 to be moved to an arbitrary position in space, for example by being rotated around a center of rotation between the X-ray tube assembly 3 and the X-ray detector 4. The inventive X-ray system 1 to 4 can be rotated in particular around centers of rotation and axes of rotation in the C-arm plane of the X-ray image detector 4, preferably around the center point of the X-ray image detector 4 and around axes of rotation intersecting the center point of the X-ray image detector 4.

The known articulated arm robot 1 has a base frame which is permanently installed on a floor for example. Attached thereto is a carousel which is rotatable about a first axis of rotation. Mounted on the carousel so as to be pivotable about a second axis of rotation is a robot rocker arm to which is attached a robot arm which is rotatable about a third axis of rotation. Mounted on the end of the robot arm is a robot hand which is rotatable about a fourth axis of rotation. The robot hand has a retaining element for the C-arm 2, said retaining element being pivotable about a fifth axis of rotation and rotatable about a sixth axis of rotation running perpendicular thereto.

The X-ray diagnostic apparatus is not dependent on the industrial robot in terms of its implementation. Conventional C-arm devices can also be used.

The X-ray image detector 4 can be a rectangular or square, flat semiconductor detector which is preferably produced from amorphous silicon (a-Si). Integrating and possibly counting CMOS detectors can also be used, however.

A patient 6 to be examined is placed as the examination subject in the beam path of the X-ray tube assembly 3 on a patient positioning table 5 so that images of the heart, for example, can be recorded. Connected to the X-ray diagnostic apparatus is a system control unit 7 having an image system 8 which receives and processes the image signals from the X-ray image detector 4 (control elements are not shown, for example). The X-ray images can then be viewed on a monitor 9.

In neuroradiology in particular, three-dimensional digital subtraction angiography (3D DSA) is a routine tool for planning and performing minimally invasive procedures. Modern neurological operating rooms also integrate this 3D capability with a rotating C-arm in order to enable pre- and intra-procedural 3D imaging of the cerebral blood vessels.

Two C-arms are widely used in neuroradiology. These are what are known as biplane systems, as described in more detail with reference to FIG. 2 as a typical interventional suite with patient table. Said systems essentially have two so-called planes, wherein the first plane 10 can consist of the X-ray diagnostic apparatus shown in FIG. 1, comprising C-arm 2, X-ray tube assembly 3 and X-ray image detector 4. A ceiling-suspended C-arm 2' having an X-ray tube assembly 3' and an X-ray image detector 4' of a second plane 12 can be provided via a ceiling fixture 11. A suspended monitor array 13 having a first display 14 for the first plane 10 and a second display 15 for the second plane 12 can also be mounted on the ceiling. A high-voltage generator 16 is provided in addition to the system control unit 7.

During an operation the brain tissue and the cerebral vessels, in particular the parts close to the surface, may be displaced after the cranium is opened.

In order to achieve a refreshed rendering of the situation it is customary in neurosurgery to perform a fluorescence angiography, an ICG angiography for example. ICG, indocyanine green, is a fluorescent dye which is employed in medicine as an optical contrast agent. In such applications it can be injected intravenously into the surface vessels. In order to fluoresce ICG is excited by means of a light source, as described for example in the dissertation at the Faculty of Medicine of the Ludwig Maximilian University in Munich titled "Validierung der Fluoreszenz-Angiographie zur intraoperativen Beurteilung and Quantifizierung der Myokardperfusion" ("*Validation of fluorescence angiography for intraoperative assessment and quantification of myocardial perfusion*") by Sabine Helena Wipper, 2006. Due to the limited penetration depth of red and infrared light only the surface structures can be reproduced by these and other optical methods.

SUMMARY OF THE INVENTION

The object of the invention is to improve the current visualization of the vessels located in the examination region in accordance with the method and the medical system for performing the method of the type cited in the introduction.

The object is inventively achieved by a method and by a device of the features recited in independent claims. Advantageous embodiments are set forth in the dependent claims.

The object is achieved according to the invention for a method by means of the following steps:

using a preoperatively recorded 3D image dataset of the examination region for generating a 3D reconstruction image of the examination region, recording at least one current 2D fluorescence image of the examination region by means of fluorescence angiography, identifying the vessels, registering the 3D image dataset with the image dataset of the 2D fluorescence or ultrasound image based on the result of the identification, overlaying the 3D reconstruction image and the 2D image, and 3D playback of the overlaid images.

The intraoperative fusion of ICG and X-ray angiography produces an enhanced, up-to-date visualization of the blood vessels lying in the examination region which is improved by comparison with the prior art.

According to the invention the preoperatively recorded 3D image dataset can be a DSA dataset.

The method can advantageously have the following steps:
S1) preoperative acquisition of a 3D image dataset of the examination region by means of digital subtraction angiography,
S2) generation of a 3D reconstruction image of the examination region from the 3D image dataset,
S3) identification of the blood vessels in the 3D reconstruction image,
S4) recording of at least one current 2D fluorescence image of the examination region by means of fluorescence angiography,
S5) identification of the blood vessels in the current 2D fluorescence image,
S6) registration of the image dataset of the 3D reconstruction image with the image dataset of the 2D fluorescence image based on the result of the identifications,
S7) overlaying of the 3D reconstruction image and the 2D fluorescence image,
S8) continuous 3D playback of the overlaid images, and
S9) repetition of steps S4) to S8) at selectable time intervals up to the end of the procedure.

It has proved advantageous if the fluorescence images of the fluorescence angiography are produced by means of ICG angiography.

According to the invention the fluorescence images can be generated continuously.

During the registration a model of attenuated displacements in terms of depth can advantageously be applied to the 3D DSA data.

The object is inventively achieved for a medical imaging system for performing the method by means of
a DSA X-ray system for generating a 3D image dataset,
an ICG angiography device for generating a current 2D image,
image storage means for buffering the 3D image dataset and the 2D fluorescence image,
a DSA image processing stage for generating a 3D reconstruction image from the 3D image dataset and identifying blood vessels in the 3D reconstruction image,
an ICG image processing stage for identifying blood vessels in the 2D fluorescence image,
a registration device for registering the 3D reconstruction image and the current 2D fluorescence image with the aid of the identification data,
an overlaying device for vessel-precise overlaying, and
a 3D display device for playing back the overlaid images.

According to the invention the device for generating a current 2D image can be an ICG angiography device for generating a current 2D fluorescence image.

Advantageously, the ICG angiography device can have a light source and a camera for capturing the fluorescence image which are integrated into a surgical microscope.

BRIEF DESCRIPTION OF THE DRAWINGS

The invention is explained in more detail below with reference to the exemplary embodiments illustrated in the drawing, in which:

FIG. 4 shows the inventive method sequence.

DETAILED DESCRIPTION OF THE INVENTION

Figure 1:
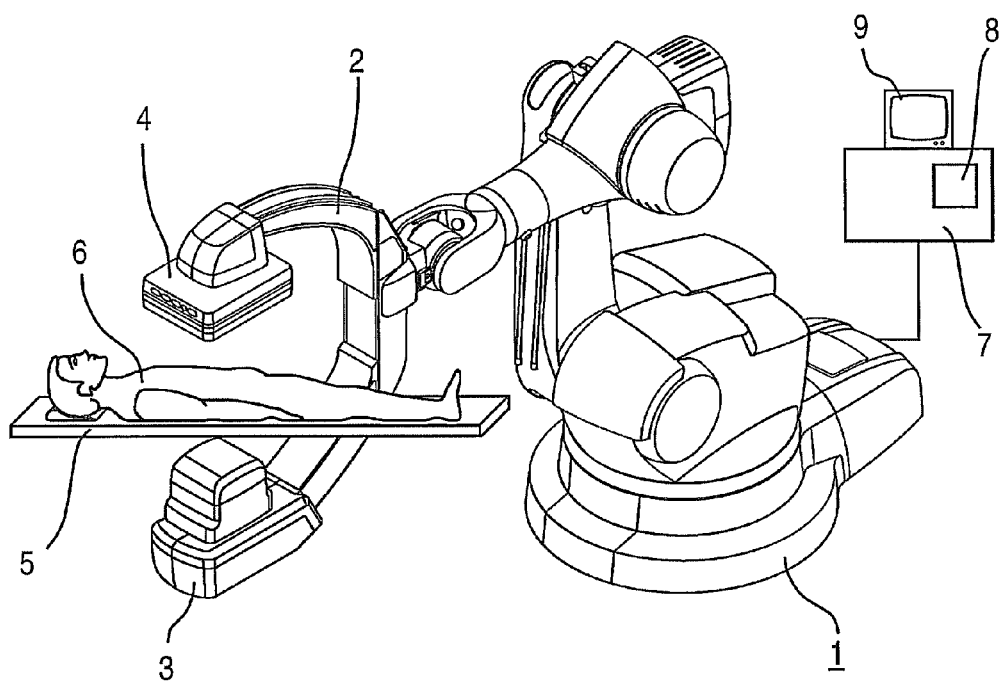
FIG. 1 shows a known X-ray C-arm system for radiology, cardiology or neurosurgery having an industrial robot as carrier device.
Figure 2:
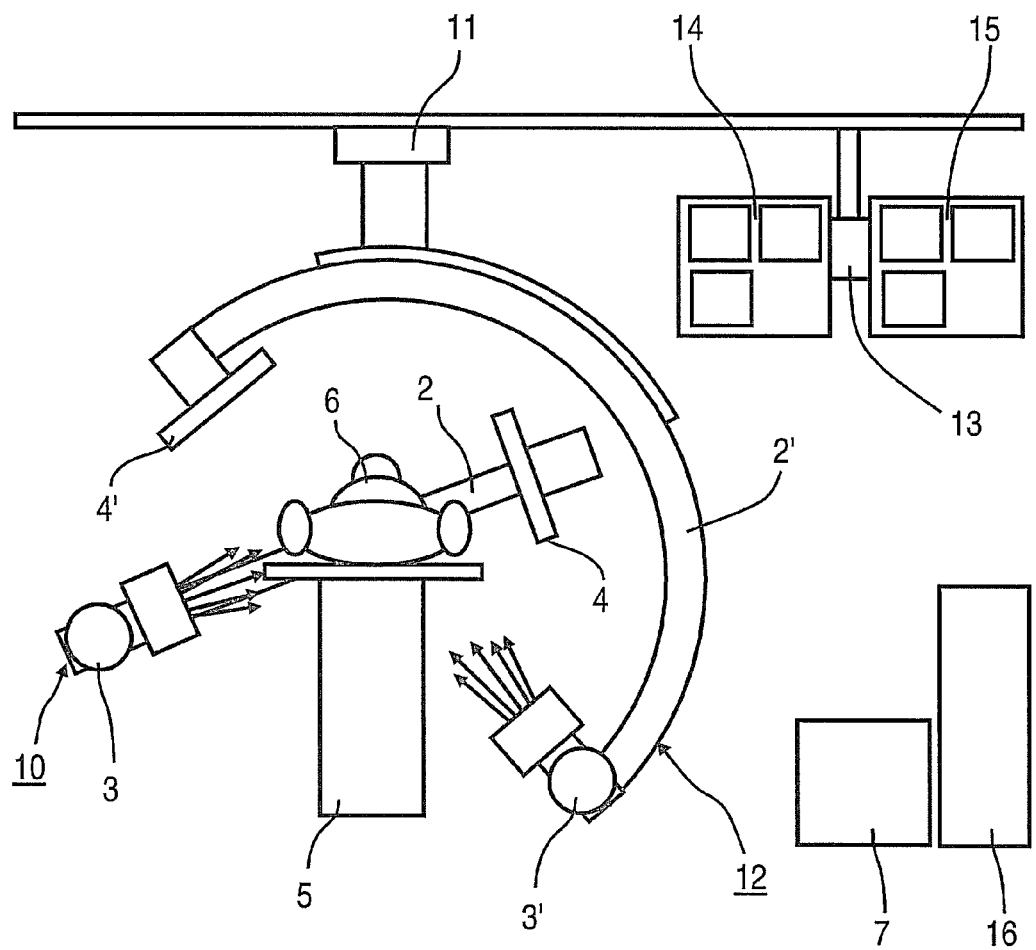
FIG. 2 shows a known biplane C-arm X-ray system for neuroradiology.
Figure 3:
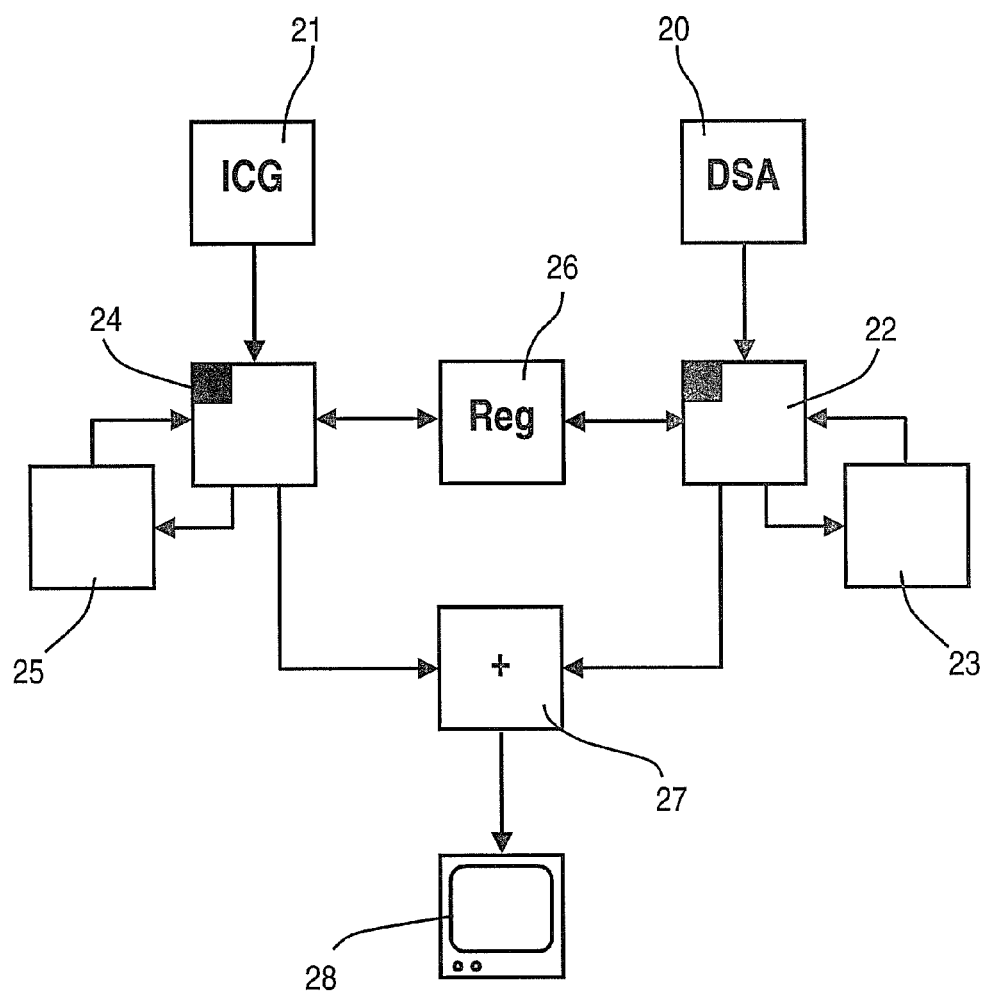
FIG. 3 shows an inventive arrangement for intraoperative fusion of ICG and X-ray angiography.

FIG. 3 shows an inventive device for intraoperative fusion of ICG and X-ray angiography comprising a DSA X-ray system 20 and an ICG angiography device 21. Connected to the DSA X-ray system 20 is a DSA image memory 22 in which firstly a recorded 3D image dataset is stored, from which, following the acquisition of the full 3D image dataset, a 3D reconstruction image is calculated by means of a DSA image processing stage 23, which image is then likewise stored in the DSA image memory 22. Subsequently the cerebral blood vessels, for example, are likewise identified in the 3D reconstruction image by means of the DSA image processing stage 23 and this data is assigned to the 3D image dataset in the DSA image memory 22.

The current 2D fluorescence image or ICG image of the ICG angiography device 21 is buffered in an ICG image memory 24. The cerebral blood vessels are also identified in the ICG image by means of an ICG image processing stage 25 and this data is assigned to the current ICG image dataset in the ICG image memory 24. Subsequently the 3D reconstruction image from the DSA image memory 22 and the current 2D fluorescence image from the ICG image memory 24 are registered by means of a registration device 26 with the aid of the identification data, overlaid in a vessel-precise manner by means of an overlaying device 27, and the preoperative 3D reconstruction image overlaid with the current 2D fluorescence image is played back on a 3D display device 28.

The inventive method sequence will now be explained in more detail with reference to FIG. 4. Prior to the (for example) surgical treatment a full 3D image dataset is preoperatively acquired by means of the DSA X-ray system 20 in a step S1). In step S2) a 3D reconstruction image is calculated from the 3D image dataset and from it the cerebral blood vessels, for example, are identified according to step S3).

In step S4), after the start of the surgical treatment, at least one current 2D fluorescence image is recorded by means of the ICG angiography device 21, or a 2D image is recorded by means of an ultrasound scanner. According to step S5) the cerebral blood vessels are identified in the 2D image of the ICG angiography device 21 or ultrasound scanner. In step S6) the image dataset of the 3D reconstruction image is registered with the image dataset of the 2D image based on the result of the identifications. The images registered in such a way are overlaid in step S7) and according to step S8) are supplied for continuous 3D playback. According to step S9) said steps S4) to S8) are repeated at selectable fixed time intervals or on request by actuation of, for example, a pushbutton up to the end of the procedure.

The basic concept underlying the present invention is the identification of the blood vessels in the ICG angiogram and in the 3D DSA image and the fixed or flexible registration so that the 3D DSA structure is consistent with the current situation found during the operation.

In order to take into account the decreasing displacement with depth, a model of attenuated displacements in terms of depth can be applied to the 3D DSA data.

This process can be repeated layer by layer if the operation penetrates further in depth. In this way the pre-procedural 3D DSA images can be updated to reflect the current situation. The 3D DSA images can also be used for predicting the vascular and parenchymal structure in the depth that is not visible for the optical imaging.

Alternatively the 3D DSA images can be repeated from time to time during the operation in order to obtain the very latest update which can be fused or registered with the ICG and serves for improving the registration in terms of depth.

The light source of the ICG angiography device 21 and the camera required for capturing the fluorescence image can be integrated into a surgical microscope for example.

Ultrasound imaging, for example, can be used instead of ICG angiography for assessing the current situation during the operation. The contrasts in ultrasound images can be intensified through the use of contrast agents, such as microbubbles for example, in order to enable registration with images of the 3D DSA images.

The registration is facilitated and improved in particular if the ultrasound scanner also supports 3D imaging.

For all these alternatives a fused rendering of the data on the monitor is essential in order to use the information more easily during the operation. Alternatively such a fusion can be implemented in the surgical microscope.

The invention claimed is:

1. An imaging method for enhancing a visualization of blood vessels in an examination region of a patient during an operation, comprising:
   generating a 3D reconstruction image of the examination region using a preoperatively recorded 3D image dataset of the examination region;
   recording at least one current 2D image of the examination region by an image recording device;
   identifying the blood vessels from the 2D image;
   registering the 3D image dataset with image dataset of the 2D image based on the identification;
   applying a model of attenuated displacements based on a depth of penetration of the operation to the preoperatively 3D image dataset during the registration;
   repeating the applying layer by layer if the operation penetrates further in the depth for updating the preoperatively recorded 3D image dataset to reflect a current situation;
   overlaying the 3D reconstruction image and the 2D image; and
   playing back the overlaid image.

2. The method as claimed in claim 1, wherein the preoperatively recorded 3D image dataset is a DSA dataset.

3. The method as claimed in claim 1, further comprising:
   preoperatively acquiring the 3D image dataset of the examination region by digital subtraction angiography;
   generating the 3D reconstruction image of the examination region from the 3D image dataset;
   identifying the blood vessels in the 3D reconstruction image;
   recording the at least one current 2D image of the examination region the image recording device;
   identifying the blood vessels in the current 2D image;
   registering image dataset of the 3D reconstruction image with image dataset of the 2D image based on the identifications;
   overlaying the 3D reconstruction image and the 2D image;
   continuously playing back the overlaid image; and
   repeating the steps of recording the at least one current 2D image to continuously playing back the overlaid image at a selectable time interval.

4. The method as claimed in claim 1, wherein the 2D image of the examination region is a 2D fluorescence image recorded by a fluorescence angiography or a 2D ultrasound image recorded by an ultrasound scanner.

5. The method as claimed in claim 4, wherein the 2D fluorescence image is recorded by an ICG angiography.

6. The method as claimed in claim 4, wherein the 2D fluorescence image is recorded continuously.

7. A medical imaging system for enhancing a visualization of blood vessels in an examination region of a patient during an operation, comprising:
   a DSA X-ray system for generating a 3D image dataset of the examination region;
   an image device for generating a current 2D image of the examination region;
   an image storage for buffering the 3D image dataset and the 2D image;
   a DSA image processing device for generating a 3D reconstruction image from the 3D image dataset and identifying the blood vessels in the 3D reconstruction image, applying a model of attenuated displacements based on a depth of penetration of the operation to the 3D image dataset during the registration, and repeating the applying layer by layer if the operation penetrates further in the depth for updating the 3D image dataset to reflect a current situation;
   an image processing device for identifying the blood vessels in the 2D image;
   a registration device for registering the 3D reconstruction image and the current 2D image based on the identification;
   an overlaying device for overlaying the 3D reconstruction image and the 2D image; and
   a 3D display device for playing back the overlaid image.

8. The medical imaging system as claimed in claim 7, wherein the image device for recording the current 2D image is an ICG angiography device and the image processing device for identifying the blood vessels in the 2D image is an ICG image processing device.

9. The medical imaging system as claimed in claim 8, wherein the ICG angiography device comprises a light source and a camera for capturing the current 2D image that are integrated into a surgical microscope.

* * * * *